(12) United States Patent
Mann

(10) Patent No.: US 6,579,222 B2
(45) Date of Patent: Jun. 17, 2003

(54) MAGNETIC TREATMENT DEVICE AND METHOD

(76) Inventor: Fred W. Mann, 222 E. Front, Waterville, KS (US) 66548

( * ) Notice: Subject to any disclaimer, the term of this patent is extended or adjusted under 35 U.S.C. 154(b) by 0 days.

(21) Appl. No.: 09/730,128

(22) Filed: Dec. 6, 2000

(65) Prior Publication Data

US 2001/0037047 A1 Nov. 1, 2001

Related U.S. Application Data

(63) Continuation-in-part of application No. 09/268,469, filed on Mar. 16, 1999, now abandoned.

(51) Int. Cl.[7] ............................................... A61N 1/00
(52) U.S. Cl. ............................... 600/15; 600/9; 128/876
(58) Field of Search ................ 600/9–15; 128/DIG. 20, 128/876; 606/27, 32; 602/19; 248/118

(56) References Cited

U.S. PATENT DOCUMENTS

| | | | | | |
|---|---|---|---|---|---|
| 3,943,912 A | * | 3/1976 | Nakayama | ..................... | 600/15 |
| 4,178,923 A | * | 12/1979 | Curlee | ................. | 128/DIG. 20 |
| 4,223,965 A | * | 11/1980 | Fairbanks | .................... | 600/14 |
| 4,915,110 A | * | 4/1990 | Kitov | ............................. | 600/11 |
| 5,165,630 A | * | 11/1992 | Connor | ..................... | 248/118.1 |
| 5,450,858 A | * | 9/1995 | Zablotsky et al. | ........... | 128/876 |
| 5,906,638 A | * | 5/1999 | Shimoda | ...................... | 607/152 |
| 6,048,303 A | * | 4/2000 | Porter | .......................... | 600/15 |
| 6,126,588 A | * | 10/2000 | Flamant et al. | ................ | 600/15 |
| 6,217,504 B1 | * | 4/2001 | Phillips | .......................... | 600/9 |
| 6,453,204 B1 | * | 9/2002 | Rhodes | ......................... | 607/149 |

* cited by examiner

Primary Examiner—Kevin Shaver
Assistant Examiner—Michael C Astorino

(57) ABSTRACT

A magnetic treatment device includes a fabric core embedded within an elastic body comprising an elastic material such as latex. Magnetic powder particles are embedded within the elastic layer and are magnetically oriented along predetermined flux lines. A first modified embodiment includes an elastic core with memory plastic and vinyl layers bonded thereto. The core and the vinyl layers have magnetic powder particles embedded therein. The magnetic flux lines can be oriented longitudinally and/or transversely with respect to the device. Other modified embodiments include mousepad and keyboard wrist support configurations. A magnetic treatment method includes the steps of embedding magnetic particles in an elastic base with a fabric core, magnetically orienting the particles and applying a strip formed by the method to a body part of a patient.

18 Claims, 6 Drawing Sheets

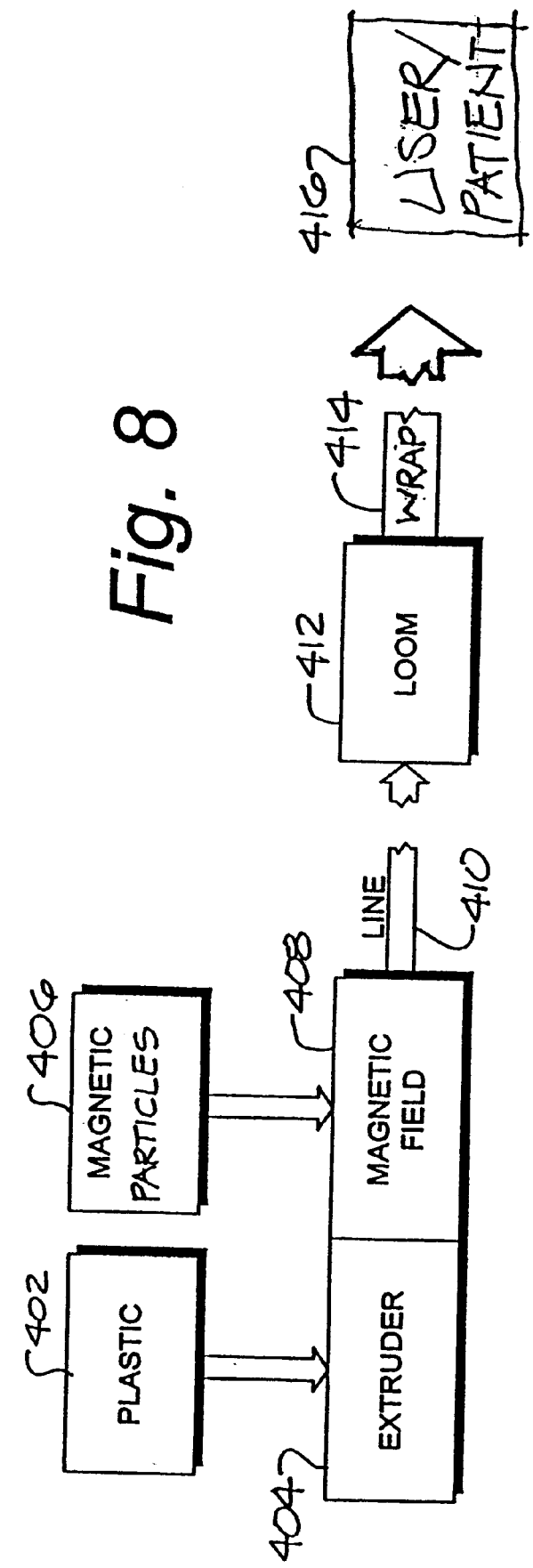

MAGNETIC TREATMENT DEVICE AND METHOD

CROSS-REFERENCE TO RELATED APPLICATION

Continuation-in-Part of U.S. patent application Ser. No. 09/268,469 filed Mar. 16, 1999, now abandoned.

BACKGROUND OF THE INVENTION

1. Field of the Invention

The present invention relates generally to magnetic flux therapy, and in particular to a magnetic treatment device and method.

2. Description of the Prior Art

Magnetism is well known to provide therapeutic benefits for a variety of conditions. For example, the Yazaki U.S. Pat. No. 4,162,672 discloses a magneto-therapeutic device with permanent magnets of ferrite. The Yazaki '672 patent discloses applications for curing stiffness with magnetic effects and with pressure-stimulation effects. The therapeutic benefits of magnetic devices are also disclosed in the Nakayama U.S. Pat. No. 3,943,912; the Baermann U.S. Pat. No. 5,017,185; the Ardizzone U.S. Pat. No. 5,277,692; and the Mitsuno et al. U.S. Pat. No. 5,304,111.

A wide variety of conditions can be treated with magnetism. For example, soreness and stiffness of patients' muscles and joints can often benefit from the application of magnetic forces. Repetitive motions are a common cause of such conditions. For example, extensive and prolonged keyboard usage is known to cause repetitive motion injuries, such as carpal tunnel syndrome. Due to the widespread use of personal computers, repetitive motion injuries induced by extensive keyboard usage are becoming increasingly common.

To counter the adverse effects of repetitive motion activities, various prosthetic devices have been proposed. These include various bands and braces designed to be worn by patients. Supports, such as wrist supports for use with keyboards, are used by many computer users. Furthermore, equipment is often designed to minimize repetitive motion injuries to users. Examples include ergonomic seating, keyboards and computer workstations. However, heretofore there has not been available a magnetic treatment device and method with the advantages and features of the present invention.

SUMMARY OF THE INVENTION

In the practice of the present invention, a magnetic treatment device is provided which includes a fabric core embedded within an elastic material, such as latex. Magnetic ferrite powder particles are deposited within the elastic material and are magnetically oriented along predetermined magnetic flux lines. Alternative embodiments include vinyl layers and memory plastic layers laminated over a latex core with magnetized powder particles deposited therein. The magnetic treatment device of the present invention can be configured as a mousepad, as a wrist support for use with a keyboard and in various other configurations.

In the practice of the method of the present invention, an elastic material, such as latex, is poured over a fabric core in a glass vessel. Magnetic ferrite, rare earth or ceramic powder particles deposited in the elastic material are positioned and oriented by a magnet placed beneath the vessel. In an alternative embodiment of the present invention, a plastic line with magnetic powder particles embedded therein is extruded, and the magnetized particles are oriented with a magnet. The line is then woven into various desired configurations, such as elastic bands.

OBJECTS AND ADVANTAGES OF THE INVENTION

The principal objects and advantages of the present invention include: providing a magnetic device; providing such a device with a resilient core; providing such a device with magnetic ferrite, rare earth or ceramic powder particles embedded in the core; providing such a device with a fabric base material embedded in a latex core; providing such a device with magnetic vinyl layers bonded to the core; providing such a device with memory plastic layers for maintaining the device in a predetermined configuration; providing such a device which is configured as a mousepad; providing such a device which is configured as a wrist support for use in conjunction with a keyboard; providing such a device which is economical to manufacture, efficient in operation, capable of a long operating life and particularly well adapted for the proposed usage thereof; and providing methods of magnetic treatment and for providing magnetic treatment devices.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 8 is a schematic block diagram of a system for producing magnetic treatment devices and for practicing the magnetic treatment method of the present invention.

DETAILED DESCRIPTION OF THE PREFERRED EMBODIMENTS

I. Introduction and Background

Figure 1:
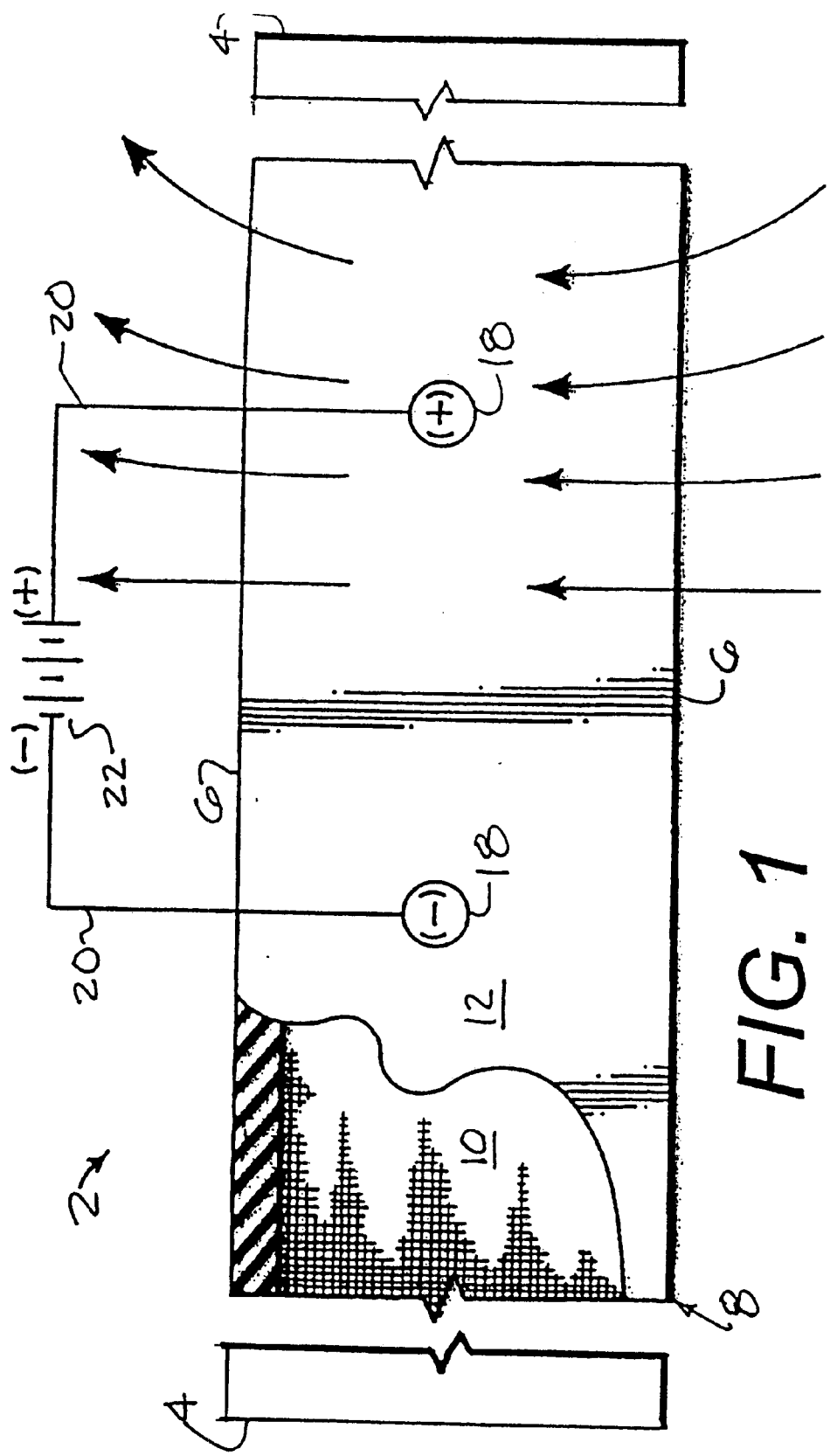
FIG. 1 is a plan view of a magnetic treatment device embodying the present invention, with portions broken away to reveal internal construction.
Figure 2:
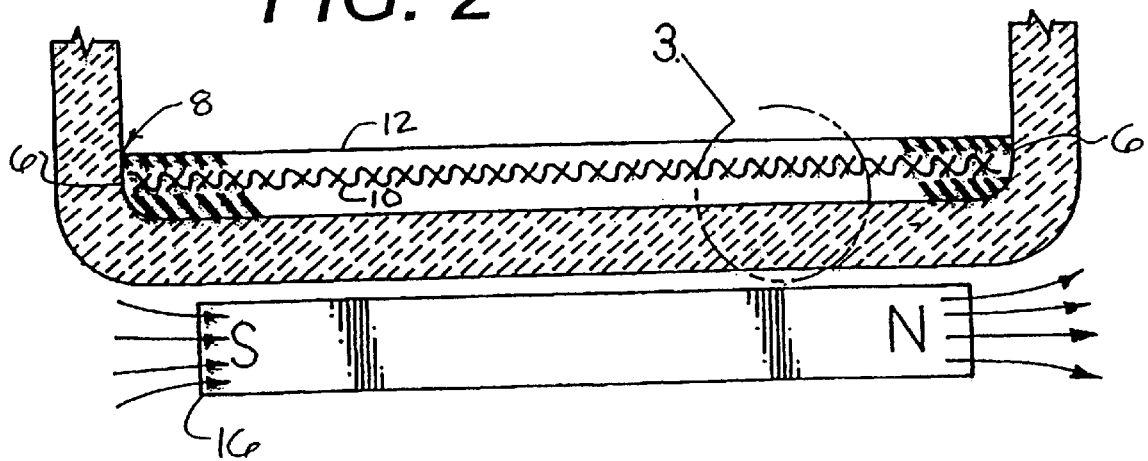
FIG. 2 is a vertical, transverse, cross-sectional view of the device, shown in a forming vessel placed over a magnet in a system for practicing the method of the present invention.
Figure 3:
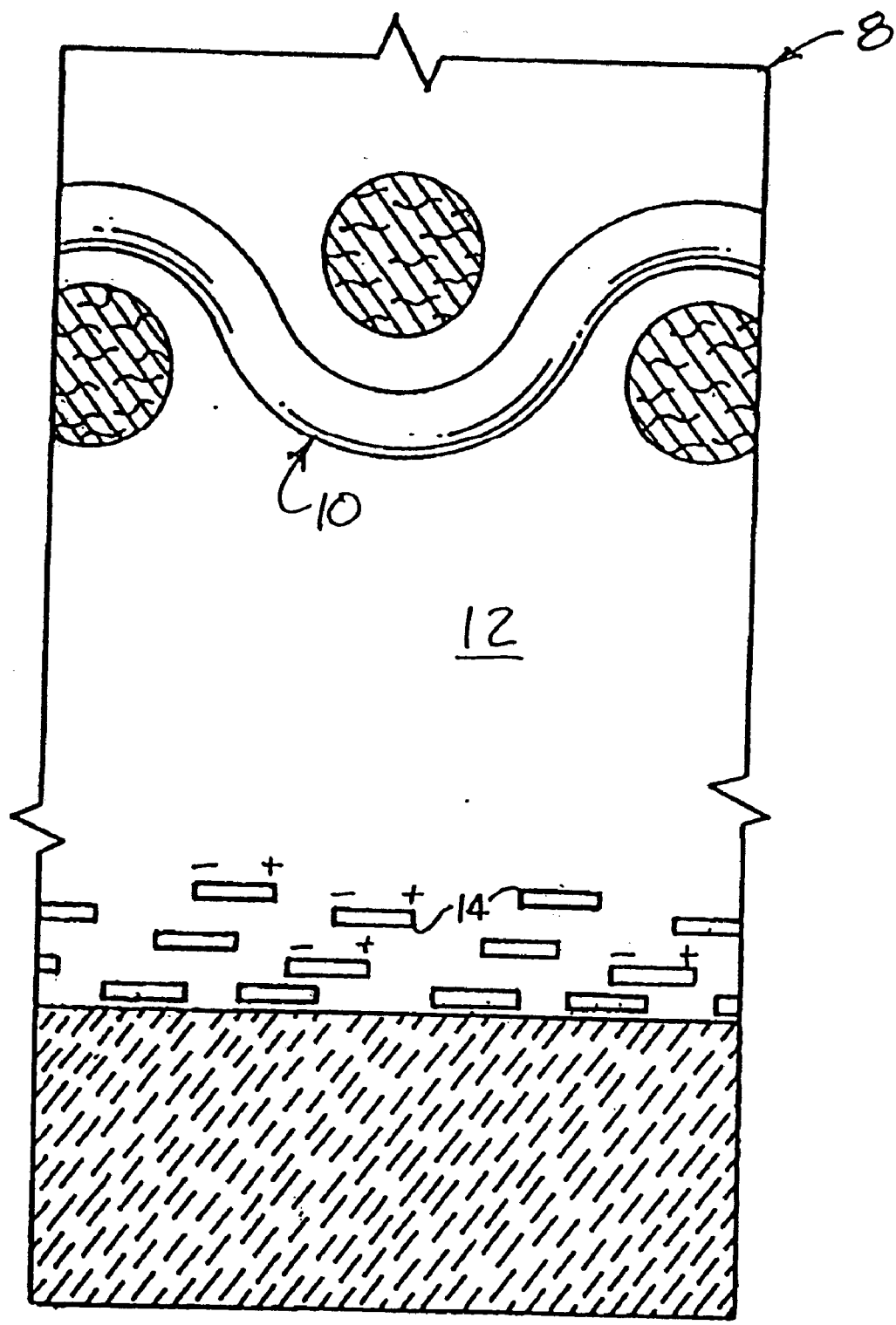
FIG. 3 is an enlarged, fragmentary detail taken generally within circle 3 in FIG. 2 and showing the construction of the device.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Magnetized Elastic Wrap 2

The reference numeral 2 generally designates a magnetic elastic wrap embodying the present invention. Without limitation on the generality of useful configurations of the present invention, the elastic wrap 2 has the general configuration of an elongated strip with opposite ends 4 and opposite side margins 6. The elastic wrap 2 comprises a body 8 with a fabric (natural or synthetic) base 10 coated with a layer of latex 12. Embedded within the latex layer 12 are ferrite, rare earth or ceramic magnetic powder particles 14, which preferably have been subjected to a magnetic field producing device 16 whereby their polarities are oriented in a predetermined orientation. For example, the magnetic powder particles 14 can be magnetically aligned along orientations which extend transversely to, longitudinally with or perpendicular (normal) to the body 8. The magnetic powder particles 14 can comprise any suitable magnetically-polarized material. For example, suitable magnetic ferrite powders are available from Hoosier Magnetics, Inc. of Holland, Ohio 43528. Various formulations of magnetic powders are available, including barium ferrite, strontium ferrite, rare earth ceramic powders, etc. The magnetic material can be chosen for its suitability for particular applications of the elastic wrap 2. Likewise, the fabric base 10 and the latex layer 12 can be chosen from a variety of suitable materials in order to achieve the desired characteristics of elasticity.

In operation, the wrap 2 is designed for wrapping around a portion of the human body, such as the waist, neck, wrists, ankles, knees, elbows, etc. The magnetic flux from the wrap 2 can thus be projected into various joints, muscles, ligature, etc. of the human body in order to avail the person wearing the wrap 2 of the benefits of such magnetic flux. The magnetic forces associated with the magnetic flux from the wrap 2 can be used for securing the wrap 2 to itself, for example, by overlapping the wrap ends 4. Various other fasteners and fastening techniques can also be used for securing the wrap 2 in place.

The proportions of the fabric base 10 and the latex layer 12, as well as their compositions, can vary considerably within the scope of the present invention. For example, a breathable magnetic elastic wrap could be constructed by employing a greater amount of fabric with respect to the elastic material. Suitable breathable, elastic fabrics are commercially available and can be magnetized according to the techniques disclosed herein.

Optional electrodes and leads 18, 20 respectively are shown in FIG. 1 and are adapted for administering an electrical current to a patient whereby the magnetic elastic wrap 2 can be used in conjunction with electrotherapy. The electrodes 18 are connected by the leads 20 to a suitable electrical current source, such as a battery 22.

III. Second Embodiment Magnetic Treatment Device 102

Figure 4:
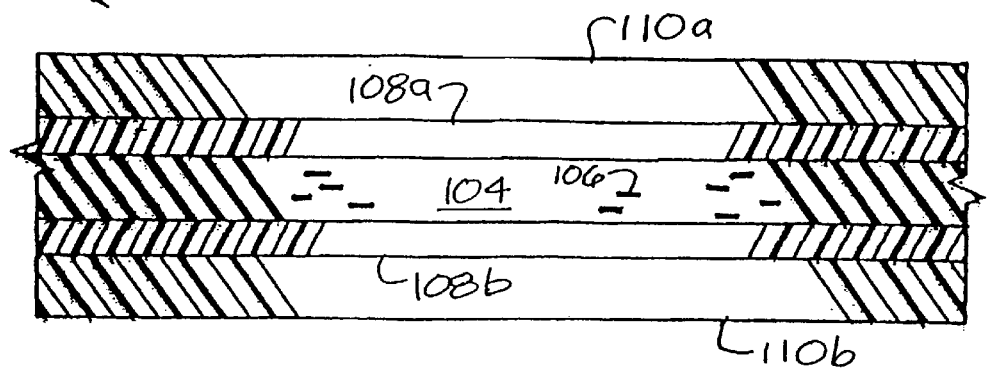
FIG. 4 is a fragmentary, vertical, cross-sectional view of a magnetic treatment device comprising a first modified embodiment of the present invention.
Figure 5A:
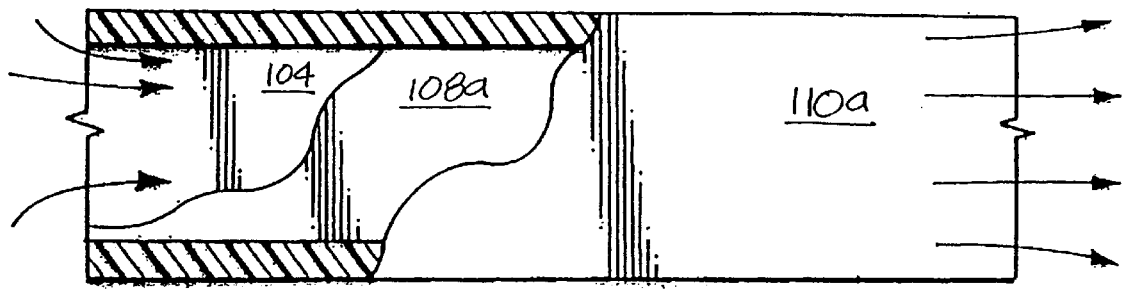
FIG. 5a is a plan view thereof with magnetic flux lines oriented longitudinally.
Figure 5B:
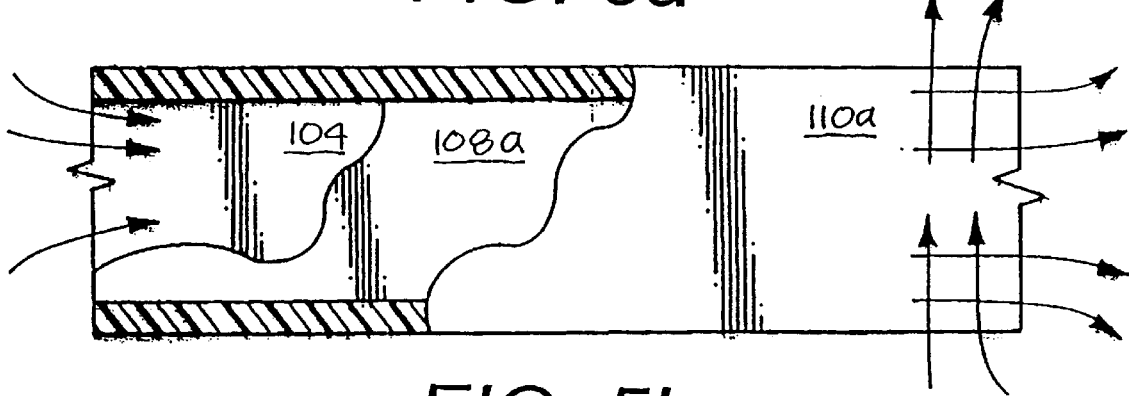
FIG. 5b is a plan view thereof with the magnetic flux lines oriented both longitudinally and transversely.

A magnetic treatment device 102 comprising a second embodiment of the present invention is show in FIGS. 4, 5a and 5b and includes a latex core 104 with magnetized ferrite powder particles 106 embedded therein. First and second layers of plastic 108a,b are secured to the latex core 104 on either side thereof. The plastic layers 108a,b preferably comprise a memory-type plastic adapted for retaining a preset shape or configuration and further adapted for reshaping and reconfiguration.

First and second magnetic vinyl outer layers 110a,b are bonded to the intermediate plastic layers 108a,b. The magnetism sources of the core 104 and the outer vinyl layers 110a,b can be magnetically aligned whereby they produce generally parallel lines of magnetic flux (FIG. 5a), whereby a person wearing the device 102 will receive flux from the counter and core magnetic layers 110a,b and 104, which will result in greater flux density due to the flux force lines emanating from multiple magnetic layer sources. The benefits of magnetic flux on a person wearing the device 102 can thus be enhanced due to the greater flux emanating from multiple magnetic layers as opposed to a single layer. Alternatively, the magnetic flux force lines can extend perpendicularly or in skewed relationship with respect to each other (FIG. 5b). The intermediate layers 108a,b of memory plastic facilitate forming the magnetic treatment device 102 in a desired configuration, such as a wrist band, bracelet, knee wrap, belt, neck brace, etc. The device 102 can thus be repeatedly worn and removed by a person and will generally return to its previous configuration.

IV. Third Embodiment Magnetic Treatment Device 202

Figure 6:
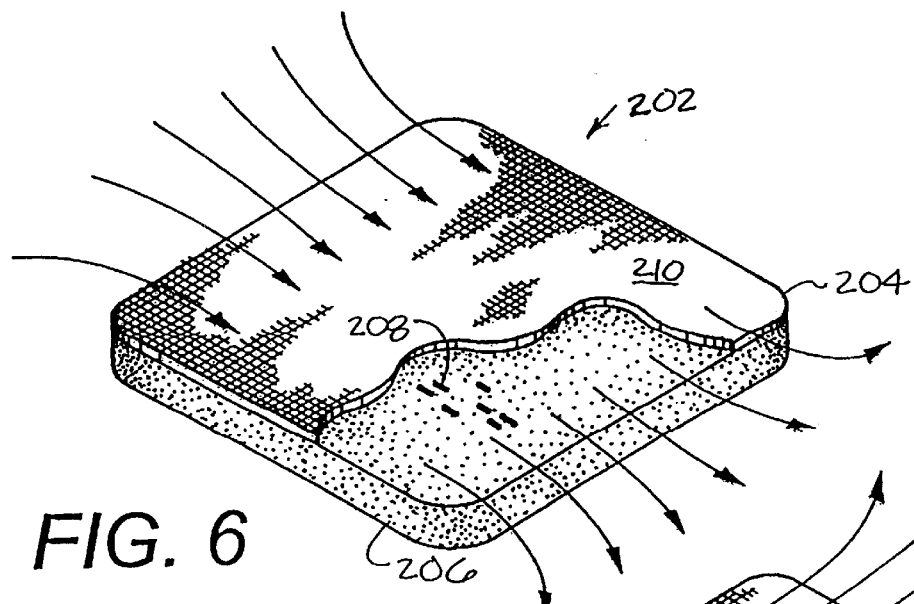
FIG. 6 is an upper perspective view of a second modified embodiment of the present invention, shown configured as a mousepad.

The reference numeral 202 generally designates a third embodiment magnetic treatment device as shown in FIG. 6. The magnetic treatment device 202 comprises a mousepad 204 with a foam layer 206 embedded with magnetic powder particles 208. A fabric cover 210 is bonded to the foam layer 206 in covering relation thereover. The magnetic treatment device 202 produces magnetic flux for treating the hands and wrists of computer users.

V. Fourth Embodiment Magnetic Treatment Device 302

Figure 7:
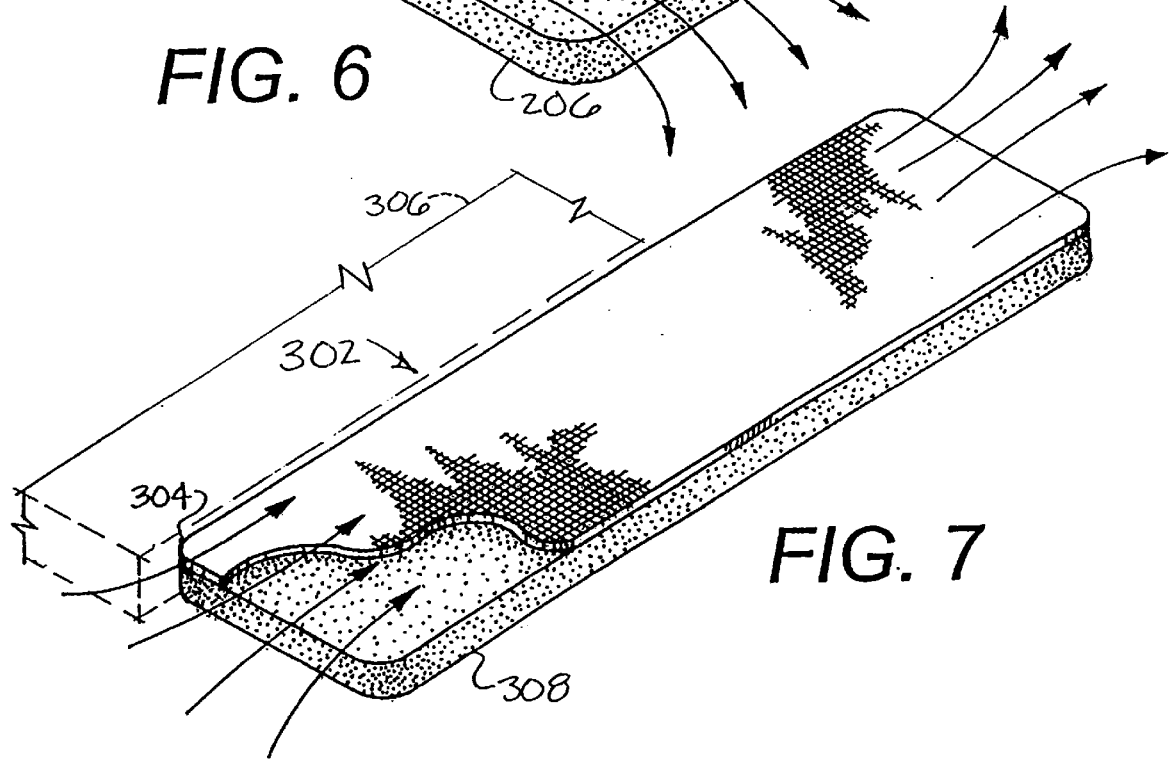
FIG. 7 is an upper perspective view of a third modified embodiment of the present invention, shown configured as a wrist support.

The reference numeral 302 generally designates a fourth embodiment magnetic treatment device comprising a wrist rest 304 for placement in front of a computer keyboard 306, as shown in FIG. 7. The wrist rest 304 includes a foam core 308 embedded with magnetic powder particles 310 and covered with a fabric cover 312 bonded to the foam core 308. The magnetized wrist rest 304 subjects the wrists of the computer user to magnetic flux. Since a number of repetitive motion type injuries and conditions are associated with extensive keyboard operation, the wrist rest 304 has the potential for providing considerable benefit to users of computers and other devices involving constant repetitive motion.

VI. Magnetic Treatment Method and Method for Producing Treatment Device

FIG. 8 shows a system for producing a magnetic treatment device and a magnetic treatment method, which embody the present invention. Plastic 402 is injected into an extruder 404, which also receives magnetic particles 406. The magnetic particles 406 are embedded in the plastic and are subjected to a magnetic field 408 for magnetic alignment. A line 410 is formed by the extruder 404 and generally comprises plastic with magnetic particles 406 embedded therein and oriented along predetermined magnetic flux lines.

The magnetized plastic line 410 can be fed to a loom 412 for weaving into various magnetic treatment devices, such as a wrap 414. The wrap 414 can be applied to a user 416.

It is to be understood that while certain forms of the present invention have been illustrated and described herein, it is not to be limited to the specific forms or arrangement of parts described and shown.

What is claimed and desired to be secured by Letters Patent is as follows:

1. A flexible, elastic, magnetic treatment device adapted for mounting on the body of a user, which comprises:

a) a latex core;

b) first and second magnetized, vinyl layers bonded to the core on opposite sides thereof; and c) magnetized particles embedded in said core, said particles being magnetically aligned in a consistent, uniform predetermined orientation generally along or parallel to a single axis oriented generally parallel to the surfaces of the device throughout said core.

2. The invention according to claim 1, which includes:
   a) said device having an elongated, strip-like configuration with parallel, opposite sides and first and second ends.

3. The invention according to claim 2, which includes:
   a) said magnetic particles in said core being substantially magnetically oriented transversely with respect to said strip.

4. The invention according to claim 2, which includes:
   a) said magnetic particles in said core being substantially magnetically oriented longitudinally with respect to said strip.

5. The invention according to claim 2, which includes:
   a) said vinyl layers being magnetically oriented transversely.

6. The invention according to claim 2, which includes:
   a) said vinyl layers being magnetically oriented longitudinally.

7. The invention according to claim 2, which includes:
   a) said magnetic particles in said core and said magnetized vinyl layers being magnetically oriented transversely with respect to each other.

8. The invention according to claim 2, which includes:
   a) first and second plastic liners each located intermediate a respective vinyl layer and said latex core.

9. A treatment method for applying magnetic force to a patient, which comprises the steps of:
   a) assembling a flexible, elastic, magnetic strip with a latex core and a vinyl layer bonded to said latex core;
   b) embedding magnetic particles in said core;
   c) embedding magnetic particles in said vinyl layer;
   d) magnetically aligning the magnetic particles in said core in a consistent, uniform predetermined orientation generally along or parallel to a single axis oriented generally parallel to the surfaces of the device throughout said core;
   e) magnetically aligning the magnetic particles in said vinyl strip in a consistent, uniform predetermined orientation generally along or parallel to a single axis oriented generally parallel to be surfaces of the device throughout said core; and
   f) applying said device to a patient.

10. The method according claim 9, which includes the additional steps of:
    a) providing said device with a layer of memory-type plastic; and
    b) shaping said device to a desired configuration for placement on a patient.

11. The method according to claim 9, which includes the additional step of:
    a) subjecting said device to microwave radiation.

12. The method according to claim 9, which includes the additional step of:
    a) subjecting said device to a magnetizing force.

13. A flexible, elastic, magnetic treatment device adapted for expanding engagement with the body of a user, which comprises:
    (a) an elastic material adapted for stretching and/or compressing in conformity to the user;
    (b) a magnetic flux source embedded in the elastic material and generally magentically aligned in a consistent, uniform predetermined orientation generally along or parallel to a single axis;
    (c) positive and negative electrodes mounted on said device in spaced relation, wherein positive and negative electrodes are adapted to administer an electrical current to said body of a user; and
    (d) positive and negative leads connected to said positive and negative electrodes respectively, said leads being adapted for connection to an electrical power source.

14. The invention according to claim 13 wherein said material is multi-directional flexible and elastic.

15. The invention according to claim 13, which includes:
    a) said material comprising latex; and
    b) a second flexible, elastic material bonded to said latex material.

16. The invention according to claim 13, which includes a second material comprising fabric.

17. The invention according to claim 13 wherein said device comprises a mousepad.

18. The invention according to claim 13 wherein said device comprises a wrist support for a keyboard.

* * * * *